(12) United States Patent
May et al.

(10) Patent No.: US 12,193,758 B2
(45) Date of Patent: Jan. 14, 2025

(54) SURGICAL SYSTEM HAVING ASSISTED NAVIGATION

(71) Applicant: Biomet Manufacturing, LLC, Warsaw, IN (US)

(72) Inventors: Brian M. May, Orange, CT (US); William Hartman, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 277 days.

(21) Appl. No.: 17/351,689

(22) Filed: Jun. 18, 2021

(65) Prior Publication Data
US 2021/0307842 A1    Oct. 7, 2021

Related U.S. Application Data

(63) Continuation of application No. 15/497,838, filed on Apr. 26, 2017, now Pat. No. 11,058,495.
(Continued)

(51) Int. Cl.
*A61B 34/20*     (2016.01)
*A61B 5/06*     (2006.01)
(Continued)

(52) U.S. Cl.
CPC .............. *A61B 34/20* (2016.02); *A61B 5/064* (2013.01); *A61B 50/26* (2016.02); *A61B 50/33* (2016.02);
(Continued)

(58) Field of Classification Search
None
See application file for complete search history.

(56) References Cited

U.S. PATENT DOCUMENTS

| 5,792,147 A | 8/1998 | Evans et al. |
| 7,840,256 B2 | 11/2010 | Lakin et al. |

(Continued)

FOREIGN PATENT DOCUMENTS

| WO | WO-02099332 A1 | 12/2002 |
| WO | WO-2013055707 A1 | 4/2013 |

(Continued)

OTHER PUBLICATIONS

"European Application Serial No. 17722587.7, Communication Pursuant to Article 94(3) EPC mailed Jun. 21, 2022", 4 pgs.
(Continued)

*Primary Examiner* — Serkan Akar
*Assistant Examiner* — Aminah Asghar
(74) *Attorney, Agent, or Firm* — SCHWEGMAN LUNDBERG & WOESSNER, P.A.

(57) ABSTRACT

A surgical navigation system comprises a computer system, a tracking system and a projector. The computer system includes instructions for performing a surgical plan. The tracking system is electronically connected to the computer system and has a viewing area in which markers can be located within a three-dimensional space relative to the viewing area. The projector is electronically connected to the computer system and has a beam projectable into the viewing area to display a step of the surgical plan based on a location of a marker. A method for guiding a surgical instrument comprises tracking a surgical instrument within a three-dimensional space using a computer-operated tracking system, matching the surgical instrument to a step in a surgical plan for conducting the surgical procedure using the surgical instrument, and projecting a visual instruction into the three-dimensional space for the step in the surgical plan related to the instrument.

17 Claims, 6 Drawing Sheets

Related U.S. Application Data

(60) Provisional application No. 62/328,337, filed on Apr. 27, 2016.

(51) Int. Cl.
    *A61B 34/00*     (2016.01)
    *A61B 50/26*     (2016.01)
    *A61B 50/33*     (2016.01)
    *A61B 90/00*     (2016.01)
    *A61B 90/90*     (2016.01)
    *A61B 5/00*     (2006.01)
    *A61B 90/50*     (2016.01)

(52) U.S. Cl.
    CPC .............. *A61B 90/37* (2016.02); *A61B 90/39* (2016.02); *A61B 90/90* (2016.02); *A61B 5/749* (2013.01); *A61B 2034/2046* (2016.02); *A61B 2034/2051* (2016.02); *A61B 2034/2055* (2016.02); *A61B 2034/2057* (2016.02); *A61B 2034/2065* (2016.02); *A61B 34/25* (2016.02); *A61B 2090/061* (2016.02); *A61B 2090/0804* (2016.02); *A61B 2090/366* (2016.02); *A61B 2090/376* (2016.02); *A61B 2090/3764* (2016.02); *A61B 2090/502* (2016.02)

(56) References Cited

U.S. PATENT DOCUMENTS

| | | | |
|---|---|---|---|
| 8,571,637 B2 | 10/2013 | Sheffer et al. | |
| 8,876,830 B2 | 11/2014 | Hodorek et al. | |
| 9,847,044 B1 | 12/2017 | Foster | |
| 11,058,495 B2 | 7/2021 | May et al. | |
| 2002/0082498 A1* | 6/2002 | Wendt | G16H 40/67 348/E13.059 |
| 2005/0195587 A1 | 9/2005 | Moctezuma De La Barrera et al. | |
| 2005/0281465 A1 | 12/2005 | Marquart et al. | |
| 2006/0142739 A1* | 6/2006 | DiSilestro | A61B 90/90 606/1 |
| 2007/0038059 A1* | 2/2007 | Sheffer | A61B 90/36 600/407 |
| 2007/0073136 A1 | 3/2007 | Metzger | |
| 2007/0142824 A1 | 6/2007 | Walker et al. | |
| 2008/0306490 A1 | 12/2008 | Lakin et al. | |
| 2013/0060146 A1 | 3/2013 | Yang et al. | |
| 2014/0121637 A1 | 5/2014 | Boyden et al. | |
| 2015/0090254 A1* | 4/2015 | Pavalarajan | A42B 3/286 128/201.23 |
| 2015/0342697 A1 | 12/2015 | Saur et al. | |
| 2016/0000516 A1 | 1/2016 | Cheng et al. | |
| 2016/0045276 A1 | 2/2016 | Pfanner et al. | |
| 2016/0217339 A1 | 7/2016 | Zhao et al. | |
| 2016/0228191 A1 | 8/2016 | Sabczynski et al. | |
| 2017/0119329 A1* | 5/2017 | Warner | A61B 90/36 |
| 2017/0312035 A1 | 11/2017 | May et al. | |
| 2019/0086787 A1* | 3/2019 | Urey | G02B 27/0101 |

FOREIGN PATENT DOCUMENTS

| | | |
|---|---|---|
| WO | WO-2015164402 A1 | 10/2015 |
| WO | WO-2017189719 A1 | 11/2017 |
| WO | WO-2018132804 A1 | 7/2018 |

OTHER PUBLICATIONS

"European Application Serial No. 17722587.7, Response filed Nov. 2, 2022 to Communication Pursuant to Article 94(3) EPC mailed Jun. 21, 2022", 26 pgs.

"Acumen™ Surgical Navigation System, Surgical Navigation Applications", Biomet Brochure, (2003), 2 pgs.

"Acumen™ Surgical Navigation System, Understanding Surgical Navigation", Biomet Brochure, (2003), 2 pgs.

"U.S. Appl. No. 15/497,838, Advisory Action mailed Jan. 14, 2020", 2 pgs.

"U.S. Appl. No. 15/497,838, Examiner Interview Summary mailed Dec. 10, 2020", 3 pgs.

"U.S. Appl. No. 15/497,838, Final Office Action mailed Oct. 29, 2019", 37 pgs.

"U.S. Appl. No. 15/497,838, Non Final Office Action mailed Apr. 19, 2019", 35 pgs.

"U.S. Appl. No. 15/497,838, Non Final Office Action mailed Sep. 3, 2020", 38 pgs.

"U.S. Appl. No. 15/497,838, Notice of Allowance mailed Mar. 16, 2021", 13 pgs.

"U.S. Appl. No. 15/497,838, Response filed Jul. 18, 2019 to Non Final Office Action mailed Apr. 19, 2019", 14 pgs.

"U.S. Appl. No. 15/497,838, Response filed Dec. 3, 2020 to Non Final Office Action mailed Sep. 3, 2020", 17 pgs.

"U.S. Appl. No. 15/497,838, Response filed Dec. 30, 2019 to Final Office Action mailed Oct. 29, 2019", 19 pgs.

"Australian Application Serial No. 2017257887, First Examination Report mailed Feb. 14, 2019", 3 pgs.

"Australian Application Serial No. 2017257887, Response filed Jun. 27, 2019 to First Examination Report mailed Feb. 14, 2019", 21 pgs.

"Australian Application Serial No. 2017257887, Response filed Nov. 6, 2019 to Subsequent Examiners Report mailed Aug. 2, 2019", 3 pgs.

"Australian Application Serial No. 2017257887, Subsequent Examiners Report mailed Aug. 2, 2019", 4 pgs.

"European Application Serial No. 17722587.7, Response filed Jun. 21, 2019 to Office Action mailed Dec. 11, 2019", 12 pgs.

"International Application Serial No. PCT/US2017/029627, International Preliminary Report on Patentability mailed Nov. 8, 2018", 8 pgs.

"International Application Serial No. PCT/US2017/029627, International Search Report mailed Aug. 22, 2017", 6 pgs.

"International Application Serial No. PCT/US2017/029627, Written Opinion mailed Aug. 22, 2017", 6 pgs.

Stiehl, James D., et al., "Navigation and Robotics in Total Joint and Spine Surgery", Chapter 1: Basics of Computer-Assisted Orthopedic Surgery (CAOS), Springer-Verlag, L.-P. Nolte, F. Langlotz, 3-9, (2004), 12 pgs.

Stiehl, James B., et al., "Navigation and Robotics in Total Joint and Spine Surgery", Chapter 3: C-Arm-Based Navigation, Springer-Verlag, pp. 17 and 18 of Chapter w/ bibliographic information, (2004), 6 pgs.

U.S. Appl. No. 15/497,838, filed Apr. 26, 2017, Surgical System Having Assisted Optical Navigation With Dual, Projection System.

* cited by examiner

SURGICAL SYSTEM HAVING ASSISTED NAVIGATION

CLAIM OF PRIORITY

This application is a continuation of U.S. patent application Ser. No. 15/497,838, filed on Apr. 26, 2017, which claims the benefit of U.S. Provisional Patent Application Ser. No. 62/328,337, filed on Apr. 27, 2016, the benefit of priority of each of which is claimed hereby, and each of which is incorporated by reference herein in its entirety.

TECHNICAL FIELD

This document pertains generally, but not by way of limitation, to navigation systems for the performance of medical surgical procedures. More particularly, this disclosure relates to, but not by way of limitation, automated navigation assistance features.

BACKGROUND

Surgical navigation systems, also known as computer assisted surgery and image guided surgery, aid surgeons in locating patient anatomical structures, guiding surgical instruments, and implanting medical devices with a high degree of accuracy. A surgical navigation system typically includes a computer, a tracking system, and patient anatomical information. The patient anatomical information can be obtained by using an imaging mode such as fluoroscopy, computer tomography (CT) or by simply defining the location of patient anatomy with the surgical navigation system. Surgical navigation systems can be used for a wide variety of surgeries to improve patient outcomes.

To successfully implant a medical device, surgical navigation systems often employ various forms of computing technology, as well as utilize intelligent instruments, digital touch devices, and advanced 3-D visualization software programs. All of these components enable surgeons to perform a wide variety of standard and minimally invasive surgical procedures and techniques. Moreover, these systems allow surgeons to more accurately plan, track and navigate the placement of instruments and implants relative to a patient's body, as well as conduct pre-operative and intra-operative body imaging.

To accomplish the accurate planning, tracking and navigation of surgical instruments, tools and/or medical devices during a surgical procedure utilizing surgical navigation, surgeons often use "tracking arrays" that are coupled to the surgical components. These tracking arrays allow the surgeons to track the physical location of these surgical components, as well as the patient's anatomy during the surgery. By knowing the physical location of the tracking array, software associated with the tracking system can accurately calculate the position of the tracked component relative to a surgical plan image.

Surgical navigation systems, however, can be limited by the information they are provided with during the pre-operative planning stage. For example, a surgical navigation system can only guide a prosthetic implant into proper alignment as accurately as the surgical plan was pre-operatively outlined. Thus, if the surgical plan determined an implant orientation that was less than optimal for a particular patient, guided navigation of that implant will not overcome that deficiency.

Examples of surgical navigation systems are described in U.S. Pat. No. 7,840,256 to Lakin et al., U.S. Pat. No. 8,571,637 to Sheffer et al., U.S. Pat. No. 8,876,830 to Hodorek et al., U.S. Pub. No. 2005/0281465 to Marquart et al., and U.S. Pub. No. 2002/0082498 to Wendt et al.

OVERVIEW

The present inventors have recognized, among other things, that a problem to be solved can include the need for surgeons to have to look away from the anatomy of the patient and the device being implanted to perform the surgical procedure. For example, surgeons frequently must consult surgical plans that are outlined on written materials or displayed on a computer monitor. Consulting both of these forms of surgical plans requires the surgeon to look away from the surgical site. Thus, the surgeon must repeatedly reorient themselves with respect to the surgical site when aligning the prosthetic implant with the anatomy and aligning surgical instruments with the prosthetic implant and the anatomy.

The present subject matter can help provide a solution to this problem, such as by providing the surgeon with a surgical plan that is within the field of view of the surgeon, thereby allowing the surgeon to maintain focus on the surgical site and the surgical plan. For example, projectors can be used to project the surgical plan directly onto the surgical site, such as from stand-mounted or helmet-mounted projectors.

The present inventors have also recognized that it can sometimes be difficult for operating room staff to identify instruments and tools during the surgical procedure. For example, surgical trays located on stands away from the surgical site can contain many different tools and instruments. Some of these tools and instruments perform the same function and therefore have the same shape, but with slightly different dimensions, and some of the tools and instruments perform different functions, but have similar shapes. Thus, selection of the proper tool or instrument can sometimes take additional time to ensure the proper tool or instrument is identified and provided to the surgeon.

The present subject matter can help provide a solution to this problem, such as by providing the operating room staff with real-time identification markers while the surgical plan is being executed by the surgeon, thereby facilitating faster and more accurate identification of the tool or instrument. For example, projectors can be used to project tool and instrument identifying markers directly onto the surgical tray or onto other locations within the operating room such as the surgical site, using stand-mounted or helmet-mounted projectors.

A surgical navigation system comprises a computer system, a tracking system and a projector. The computer system has stored therein instructions for performing a surgical plan. The tracking system is electronically connected to the computer system and has a viewing area in which markers can be located within a three-dimensional space relative to the viewing area. The projector is electronically connected to the computer system and has a beam projectable into the viewing area to display a step of the surgical plan based on a location of a marker in the three-dimensional space.

A method for guiding a surgical instrument comprises tracking a surgical instrument within a three-dimensional space using a computer-operated tracking system, matching the surgical instrument to a step in a surgical plan for conducting the surgical procedure using the surgical instrument, and projecting a visual instruction into the three-dimensional space for the step in the surgical plan related to the instrument.

This overview is intended to provide an overview of subject matter of the present patent application. It is not intended to provide an exclusive or exhaustive explanation of the invention. The detailed description is included to provide further information about the present patent application.

Figure 1:
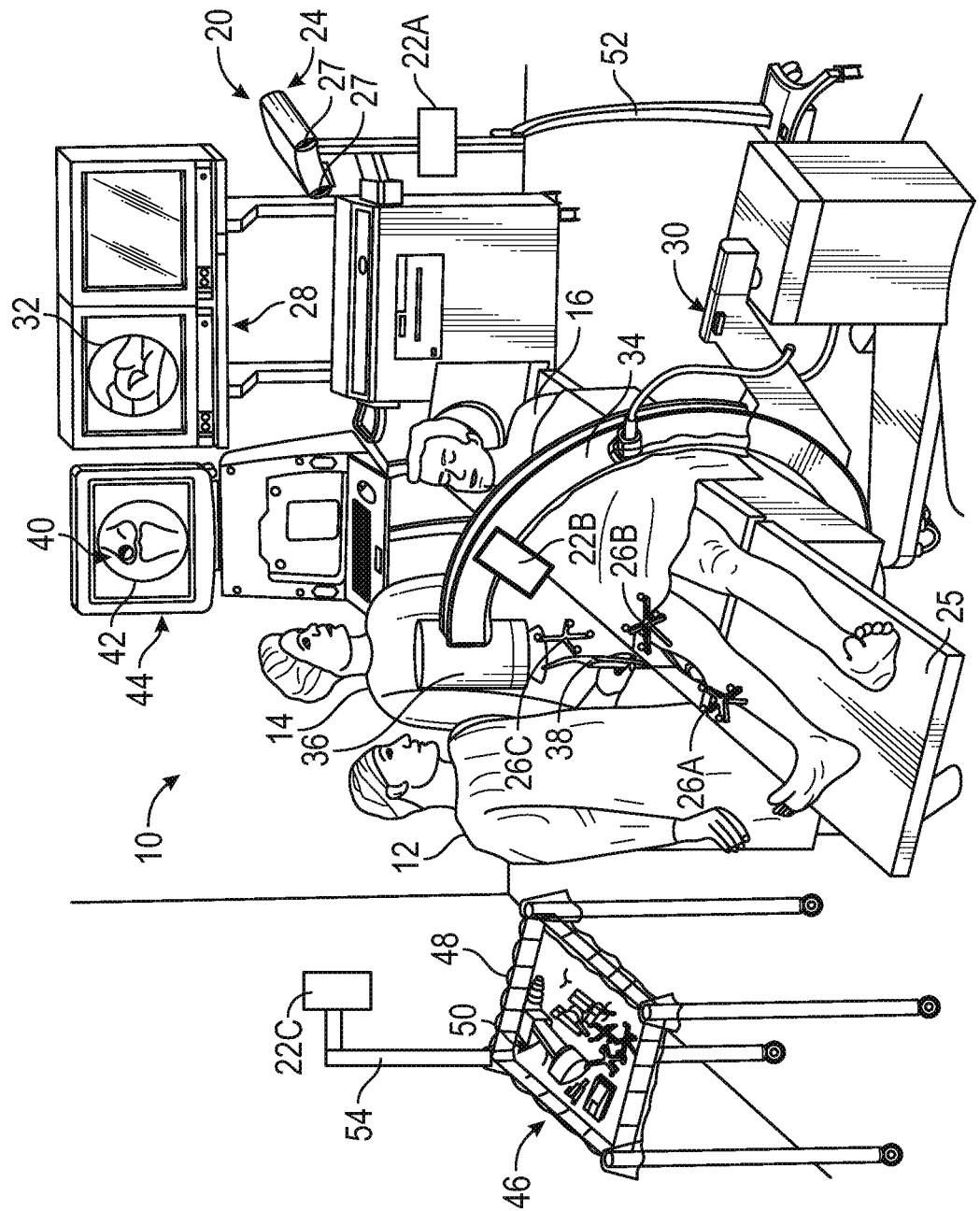
FIG. 1 is a perspective view of an exemplary operating room setup with an assisted surgical navigation system including various projectors for producing various visual instructions in conjunction with optical locators.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 shows a perspective view of operating room 10 in which surgeon 12, clinician 14 and patient 16 can be located to perform a medical procedure. Surgical navigation system 20 can also be located in operating room 10 and can include projectors 22A-22C and optical locator 24. Surgeon 12 can be aided by surgical navigation system 20 in performing knee arthroplasty, also known as knee replacement surgery, on patient 16 shown lying on operating table 25. In one example, a total knee replacement procedure can be performed. System 20 may also be used to perform any number or other types of procedures, particularly other arthroplasty procedures. One example of a surgical navigation system suitable for use with the present disclosure is described in U.S. Pat. No. 7,840,256 to Lakin et al., which is hereby incorporated herein in its entirety by this reference. Typically, before any procedure is performed, surgeon 12 and clinician 14 can develop a surgical plan that outlines steps to be performed by surgeon 12 and clinician 14 during the procedure.

Surgical navigation system 20 can have a tracking system that locates arrays, such as arrays 26A-26C, and tracks them in real-time. Surgical navigation system 20 can also includes projectors 22A-22C that project various images throughout operating room 10 to assist surgeon 12 and clinician 14 in performing the surgical plan.

To accomplish the tracking, surgical navigation system 20 can include optical locator 24, which can have two CCD (charge couple device) cameras 27 that detect the positions of the arrays in space by using triangulation methods. The relative location of the tracked arrays, including the patient's anatomy, can then be shown on a computer display, such as computer display 28 for instance, to assist surgeon 12 during the surgical procedure. The arrays that are typically used can include probe arrays, instrument arrays, reference arrays, and calibrator arrays.

To accomplish the projecting, projectors 22A-22C can emit a light beam onto the various anatomy, tools and instruments connected to arrays 26A-26C. The light beams can project various images, such as words, icons and the like, onto patient 16 and other locations in operating room 10 to prompt surgeon 12 or clinician 14 to perform various tasks to execute the surgical plan.

Operating room 10 can include an imaging system, such as C-arm fluoroscope system 30 with fluoroscope display image 32 to show a real-time image of the patient's knee on computer display (video monitor) 28. C-arm fluoroscope system 30 can include C-arm 34 to which emitter 36 is mounted. The tracking system can also detect the location of diagnostic scope 38 including its reference array 26C, as well as reference arrays 26A and 26B, which can be attached to the patient's femur and tibia, respectively. The relative location of diagnostic scope 38 to the patient's femur is shown as reference numeral 40 on computer display image 42 of computer display (video monitor) 44. Operating room 10 can also include instrument cart 46 having tray 48 for holding a variety of surgical instruments and arrays, such as surgical drill 50.

Optical locator 24 can be positioned in operating room 10 so that cameras 26 have complete coverage of table 25 and cart 46. Projectors 22A-22C can be located at various locations throughout operating room 10 so as to be able to project onto different locations. For example, projector 22A can be mounted on camera stand 52, projector 22B can be mounted on C-arm 34 and projector 22C can be mounted on tray stand 48 using stand 54. In other examples, such that of FIG. 4, a projector can be mounted on a helmet worn by surgeon 12 or clinician 14 during the procedure.

A representation of the patient's anatomy can be acquired with an imaging system, a virtual image, a morphed image, or a combination of imaging techniques. The imaging system can be any system capable of producing images that represent the patient's anatomy such as a fluoroscope producing x-ray two-dimensional images, computer tomography (CT) producing a three-dimensional image, magnetic resonance imaging (MRI) producing a three-dimensional image, ultrasound imaging producing a two-dimensional image, and the like. A virtual image of the patient's anatomy can be created by defining anatomical points with the surgical navigation system 20 or by applying a statistical anatomical model. A morphed image of the patient's anatomy can be created by combining an image of the patient's anatomy with a data set, such as a virtual image of the patient's anatomy. Some imaging systems, such as C-arm fluoroscope 30, can require calibration. The C-arm can be calibrated with a calibration grid that enables determination of fluoroscope projection parameters for different orientations of the C-arm to reduce distortion. A registration phantom can also be used with a C-arm to coordinate images with the surgical navigation application program and improve scaling through the registration of the C-arm with the surgical navigation system. A more detailed description of a C-arm based navigation system is provided in James B. Stiehl et al., Navigation and Robotics in Total Joint and Spine Surgery, Chapter 3: C-Arm-Based Navigation, Springer-Verlag (2004).

Projectors 22A-22C can be used to project images onto patient 16 or tray 48 in order to execute the surgical plan. For example, projectors 22A and 22B can project beams with instructions for performing cuts and incisions on patient 16 at the surgical site. Projector 22C can project beams onto tray 48 to identify which tool or instrument is needed at a particular point in time while surgeon 12 is executing the surgical plan. The beamed instructions can be in the form of light beams, laser beams or the like. In other examples, holographic images can be projected.

Figure 2:
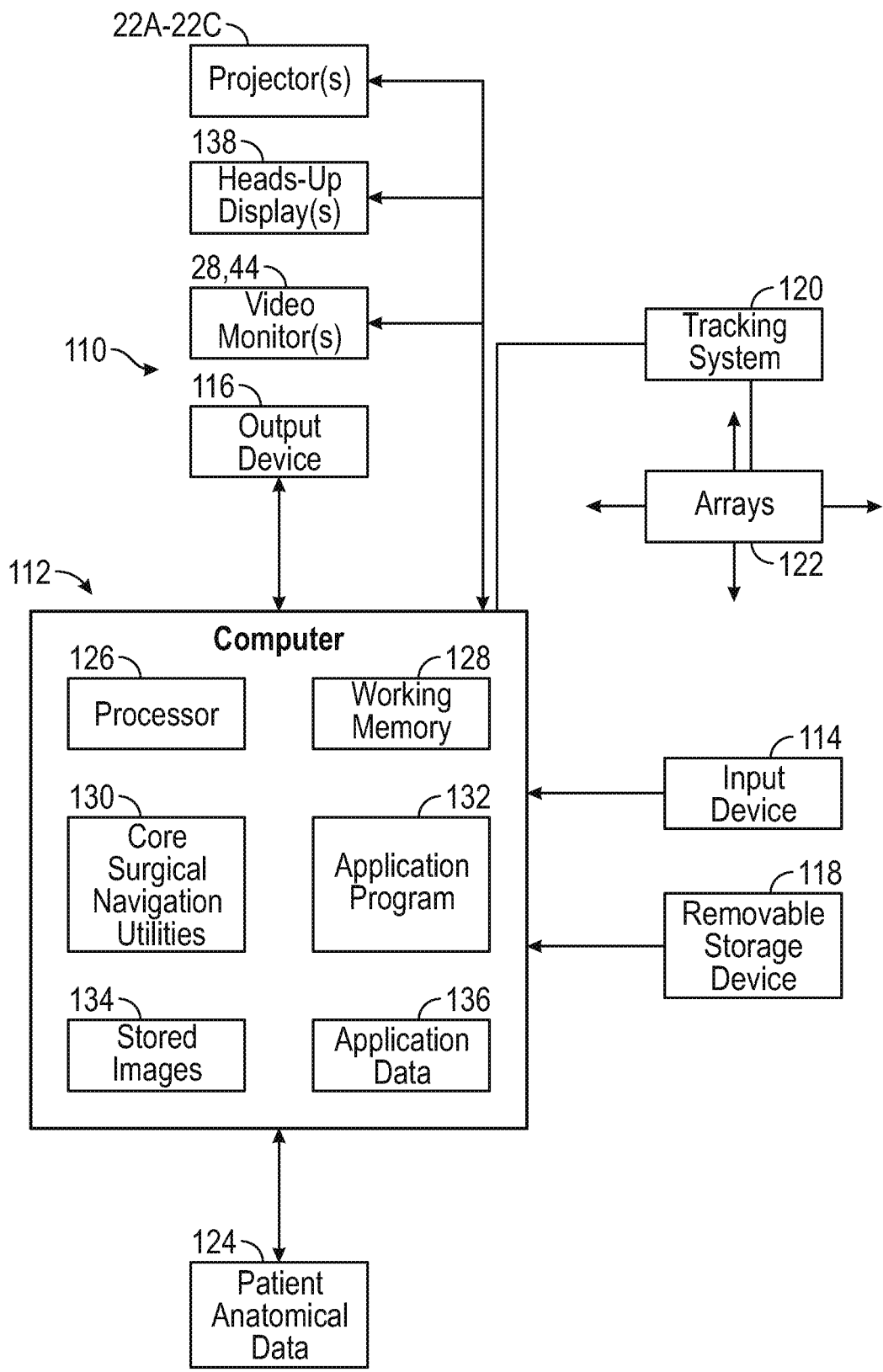
FIG. 2 is a block diagram of the assisted surgical navigation system of FIG. 1 having a tracking system and various projectors.

FIG. 2 is a block diagram of an exemplary surgical navigation system embodiment in accordance with the present teachings, such as an Acumen™ Surgical Navigation System, manufactured by EBI, L.P., Parsippany, N.J. USA, a Biomet Company. The surgical navigation system 110 can comprise computer 112, input device 114, output device 116, removable storage device 118, tracking system 120, arrays 122, and patient anatomical data 124, as further described in the brochure Acumen™ Surgical Navigation System, Understanding Surgical Navigation (2003) published by EBI, L.P. The Acumen™ Surgical Navigation System can operate in a variety of imaging modes such as a fluoroscopy mode creating a two-dimensional x-ray image, a computer-tomography (CT) mode creating a three-dimensional image, and an imageless mode creating a virtual image or planes and axes by defining anatomical points of the patient's anatomy. In the imageless mode, a separate imaging device such as a C-arm (e.g., C-arm fluoroscope system 30) is not required, thereby simplifying set-up. The Acumen™ Surgical Navigation System can run a variety of orthopedic applications, including applications for knee arthroplasty, hip arthroplasty, spine surgery, and trauma surgery, as further described in the brochure "Acumen™ Surgical Navigation System, Surgical Navigation Applications" (2003), published by from EBI, L.P. A more detailed description of an exemplary surgical navigation system is provided in James B. Stiehl et al., Navigation and Robotics in Total Joint and Spine Surgery, Chapter 1: Basics of Computer-Assisted Orthopedic Surgery (CAOS), Springer-Verlag (2004).

Computer 112 can be any computer capable of properly operating surgical navigation devices and software, such as a computer similar to a commercially available personal computer that comprises processor 126, working memory 128, core surgical navigation utilities 130, application program 132, stored images 134, and application data 136. Processor 126 can be a processor of sufficient power for computer 112 to perform desired functions, such as one or more microprocessors. Working memory 128 can be memory sufficient for computer 112 to perform desired functions such as solid-state memory, random-access memory, and the like. Core surgical navigation utilities 130 can be the basic operating programs, and include image registration, image acquisition, location algorithms, orientation algorithms, virtual keypad, diagnostics, and the like. Application program 132 can be any program configured for a specific surgical navigation purpose, such as orthopedic application programs for unicondylar knee ("uni-knee"), total knee, hip, spine, trauma, intramedullary ("IM") nail/rod, and external fixator. Stored images 134 can be those recorded during image acquisition using any of the imaging systems previously discussed (e.g., C-arm fluoroscope system 30). Application data 136 can be data that is generated or used by application program 132, such as implant geometries, instrument geometries, surgical defaults, patient landmarks, and the like. Application data 136 can be pre-loaded in the software or input by the user during a surgical navigation procedure.

Input device 114 can be any conventional computer peripheral, such as a keyboard, mouse, pointing device or camera. Input device 114 can also comprise a microphone for listening to surgeon 12, clinician 14 and patient 16. In one example, the microphone can cause projectors 22A-22C to generate visual instructions for surgeon 12 and clinician 14 based on audio calls by either of those persons.

Output device 116 can be any device capable of creating an output useful for surgery, such as a visual output and an auditory output. The visual output device can be any device capable of creating a visual output useful for surgery, such as a two-dimensional image, a three-dimensional image, a holographic image, and the like. The visual output device can be a monitor for producing two and three-dimensional images, a projector for producing two and three-dimensional images, and indicator lights. The auditory output can be any device capable of creating an auditory output used for surgery, such as a speaker that can be used to provide a voice or tone output. In particular, output devices can include projectors 22A-22C and computer displays 28 and 44. In one embodiment, a heads-up display comprising a screen or panel connected to a surgical helmet (e.g. helmet 460 of FIG. 4) onto which one of projectors 22A-22C, or another helmet-mounted projector (e.g., projector 462 of FIG. 4), can directly projects.

Removable storage device 118 can be any device having a removable storage media that would allow downloading data, such as application data 136 and patient anatomical data 124. The removable storage device can be a read-write compact disc (CD) drive, a read-write digital video disc (DVD) drive, a flash solid-state memory port, a removable hard drive, a floppy disc drive, and the like. Removable storage device 118 can include all of or portions of the aforementioned surgical plan.

Tracking system 120 can be any system that can determine the three-dimensional location of devices carrying or incorporating markers that serve as tracking indicia. An active tracking system can have a collection of infrared light emitting diode (ILEDs) illuminators that surround the position sensor lenses to flood a measurement field of view with infrared light. A passive system can incorporate retro-reflective markers that reflect infrared light back to the position sensor, and the system triangulates the real-time position (x, y, and z location) and orientation (rotation around x, y, and z axes) of an array 122 and reports the result to the computer system with an accuracy of about 0.35 mm Root Mean Squared (RMS). An example of a passive tracking system is a Polaris® Passive System and an example of a marker is the NDI Passive Spheres™, both available from Northern Digital Inc. Ontario, Canada. A hybrid tracking system can detect active and active wireless markers in addition to passive markers. Active marker based instruments can enable automatic tool identification, program control of visible LEDs, and input via tool buttons. An example of a hybrid tracking system is the Polaris® Hybrid System, available from Northern Digital Inc. A marker can be a passive IR reflector, an active IR emitter, an electromagnetic marker, and an optical marker used with an optical camera.

As is generally known within the art, implants and instruments may also be tracked by electromagnetic tracking systems. These systems locate and track devices and produce a real-time, three-dimensional video display of the surgical procedure. This can be accomplished by using electromagnetic field transmitters that generate a local magnetic field around the patient's anatomy. In turn, the localization system includes magnetic sensors that identify the position of tracked instruments as they move relative to the patient's anatomy. By not requiring a line of sight with the transmitter, electromagnetic systems are also adapted for in vivo use, and are also integrable, for instance, with ultrasound and CT imaging processes for performing interventional procedures by incorporating miniaturized tracking sensors into surgical instruments. By processing transmitted signals generated by the tracking sensors, the system is able to determine the position of the surgical instruments in space, as well as superimpose their relative positions onto pre-operatively captured CT images of the patient.

Arrays 122, which can include arrays 26A-26C, can be probe arrays, instrument arrays, reference arrays, calibrator arrays, and the like. Arrays 122 can have any number of markers, but typically have three or more markers to define real-time position (x, y, and z location) and orientation (rotation around x, y, and z axes). An array can comprise a body and markers. The body can comprise an area for spatial separation of the markers. In some embodiments, there are at least two arms and some embodiments can have three arms, four arms, or more. The arms can typically be arranged asymmetrically to facilitate specific array and marker identification by the tracking system. In other embodiments, such as a calibrator array, the body can provide sufficient area for spatial separation of markers without the need for arms. Arrays can be disposable or non-disposable. Disposable arrays can typically be manufactured from plastic and can include installed markers. Non-disposable arrays can be manufactured from a material that can be sterilized, such as aluminum, stainless steel, and the like. The markers can be removable, so they can be removed before sterilization.

Planning and collecting patient anatomical data 124 can be a process by which a clinician inputs into the surgical navigation system actual or approximate anatomical data. Anatomical data can be obtained through techniques such as anatomic painting, bone morphing, CT data input, 3-D laser scanning and other inputs, such as ultrasound and fluoroscope and other imaging systems.

Patient anatomical data 124 can also include patient-specific information relating to a particular surgical plan for patient 16. For example, the surgical plan of the surgical procedure can include the planning of various bone resections, sizes and types of implants, and various geometric requirements including relevant dimensions, such as height, width, orientation of particular features, etc. The pre-operative surgical plan can include a recommendation of particular implants and associated instruments to be used in the surgical procedure. The pre-operative surgical plan can be in the form of digital images that can be viewed interactively using a computer modeling software. The pre-operative plan can be a plan devised to obtain a healthy or as close to healthy anatomical orientation after an operative procedure. The healthy anatomy can be based on natural or pre-injury anatomy or mechanically correct or efficient anatomical orientation.

The surgical plan can include, for example, a distal femur with approved resection planes including medial and lateral anterior chamfer planes, medial and lateral anterior cut planes, medial and lateral posterior chamfer planes and medial and lateral posterior cut planes. The surgical plan can include defining a desired varus tilt to the femoral cut plane relative to the implant coordinate frame, or constraining the tibial cut plane in the flexion-extension orientation as well.

The surgical plan can include instructions for removing one or more osteophytes/protrusions from the patient's anatomy at surgeon-selected locations and depths, which, along with smoothening of the joint surfaces that receive the implant, can parallel the intra-operative joint preparation by the surgeon and improve the actual fit of a surgeon-selected implant, whether patient-specific, semi-custom, or off the shelf.

The surgical plan can also include a list or matrix of where each tool or instrument to be used during the surgical procedure is to be located at each step of the surgical plan. Thus, each step in the surgical procedure can have a unique location for each of the instruments or tools, which can then be used to determine which step needs to happen next. Thus, system 20 can then use projectors 22A-22C to direct surgeon 12 and clinician 14 in executing the surgical plan. In an example, system 20 can project an instruction or prompt for the next step in the surgical plan based on a user input from surgeon 12 or clinician 14. In another example, system 20 can project an identifying marker onto an instrument to be used in the next step of the procedure.

In another example, the list or matrix of information can include data relating to voice recognition features of navigation system 20. For example, a voice signature for each of the surgical instruments can be associated with the tool or instrument, along with its unique location, and unique visual signature (e.g. the three-dimensional geometry of each instrument. Likewise, the list or matrix can also include other information pertaining to each tool or instrument, such as a unique identifier or image for each tool or instrument, as will be discussed below.

Cameras 27 can observe the location of arrays 26A-26C, as well as other arrays within a three-dimensional space within operating room 10 within the viewing area of cameras 27. In other examples, more than one optical locator 24 can be used to determine the three-dimensional space. Positional information obtained from arrays 26A-26C corresponding to the instruments or tools associated with or attached to each array can be used by computer 112 determine an instruction to be projected by projectors 22A-22C. In particular, computer 112 can compare or correlate the location of one or more instruments or tools within the three-dimensional space and can then consult the surgical plan to determine at which step the surgical procedure is at in the surgical plan. From that comparison or correlation, computer 112 can cause projectors to project an instruction, such as an identifying marker onto an instrument or tool or a directional instruction for a tool onto patient 16, into the three-dimensional space.

Figure 3:
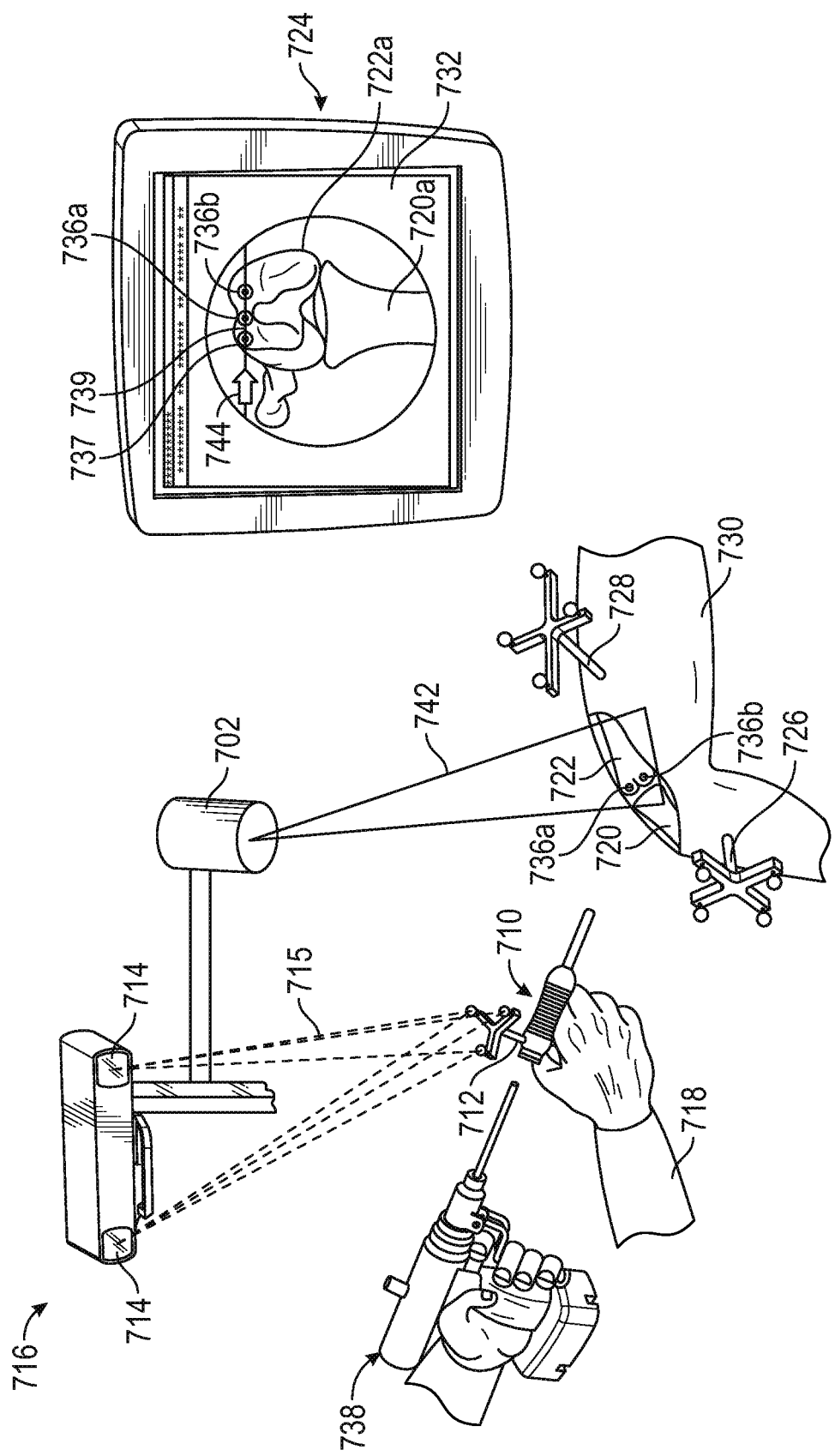
FIG. 3 is a schematic view of a stand-mounted projector used in conjunction with a stand-mounted optical locator.

FIG. 3 is a schematic view of a surgical navigation system (e.g. navigation system 20 of FIG. 1) having stand-mounted projector 702 (which may comprise projector 22A of FIG. 1 in an example) used in conjunction with optical locator 716 (which may comprise optical locator 24 of FIG. 1 in an example). Drill guide 710 can include marker array 712, which can be identified and tracked by cameras 714 (e.g. cameras 27) of optical locator 716. FIG. 3 is described with reference to using a drill guide and drill. However, the procedures of the present application may be used with any type of surgical tool, instrument, guide or the like. For example, in a total knee arthroplasty, arrays can be used in conjunction with 4-in-1 cut blocks and other femoral and tibial cutting and resection guides.

As surgeon 718 moves drill guide 710 relative to bones 720 and 722, the tracking system (e.g. navigation system 20 of FIG. 1 in an example) can locate and track marker array 712 in real-time. In FIG. 3, the optical path/measurement field of the tracking system is represented by dashed lines 715. To accomplish this, cameras 714 of optical locator 716 can detect the position of marker array 712 in space by using triangulation methods. The relative location of marker array 712 can then be shown on surgical plan image 732 on computer display 724 (e.g. computer display 44).

The tracking system can detect the location of drill guide 710 relative to bones 720, 722 by referencing the position of marker array 712 as it moves with respect to reference arrays 726 and 728, which can be fixably attached to the tibia and femur of patient 730. As shown in FIG. 3, the position of drill guide 710 can be displayed on surgical plan image 732 as drill location icon 737. According to this illustration, drill location icon 737 is shown positioned over the distal condyle of surgical bone 722, such that drilling will occur from distal to proximal on the distal condyle of bone 722. By viewing drill location icon 737 on surgical plan image 732, surgeon 718 can determine which direction to move drill guide 710 so that it aligns with either of surgical target sites 736a or 736b on surgical bone images 720a, 722a (which respectively correspond to bones 720, 722). For instance, in this illustrated embodiment, surgeon 718 can move drill guide 710 immediately to the right along line 739 to align drill location icon 737 with surgical target site 736a. To locate surgical target site 736a, the distal most point on the distal medial femoral condyle may be referenced by the surgeon and/or the computer tracking system. In certain exemplary embodiments, surgical target site 736a can be identified by modeling the medial distal femoral condyle through a "painting" or imaging technique which allows the computer system to determine the distal most point on bone 722.

Surgeon 718 could look away from the surgical site at bones 720 and 722 to look at computer display 724. However, in the system of the present application, projector 702 can project drill location icon 737 and surgical target sites 736a and 736b directly onto bone 722 using beam 742. Surgeon 718, thus, does not have to look away from the surgical site. This allows surgeon 718 to remain mentally focused on the surgical procedure and visually focused on bones 720 and 722.

In one example, the surgical plan is projected onto the anatomy based on the pre-operative surgical plan based on the location of the anatomy using arrays 726 and 728. In another example, navigation system 20 can operate without the use of arrays, particularly without arrays 726 and 728. Pre-operatively obtained images of tibia 720 and femur 722 can be compared to real-time images of tibia 720 and femur 722 obtained by optical locator 716. Pre-identified markers, such as anatomical features on both or one of tibia 720 and femur 722 in the pre-operatively obtained images can then be compared to the real-time images so that projector 702 can change the location of where beam 742 is projected to again align the projected surgical plan with the anatomy. Alternatively, tibia 720 and femur 722 can be put back into the previous orientation, or optical locator 716 can be reoriented to align the real-time image with the pre-operatively obtained images based on a comparison of the pre-operatively obtained images and the real-time images. In another example, projector 702 can project a virtual marker using beam 742 that is identifiable by optical locator 716. As optical locator 716 detects a change in location of the virtual marker relative to a pre-identified marker in the real-time images, projector 702 can adjust the location of the virtual marker back to the pre-identified marker, adjusting the surgical plan projected by beam 746 along with it. In any of these scenarios, arrays 726 and 728 can be eliminated, which benefits the patient and reduces cost. First, tibia 720 and femur 722 do not need to be subjected to any incisions, drilling or cutting to receive arrays 726 and 728, which eliminates a potential risk of fracturing the bone. Additionally, cost associated with using arrays 726 and 728 can be eliminated, as well as costs associated with correcting issues developing from holes in bones produced to secure arrays 726 and 728.

In additional examples, the surgical target site can be identified by referencing the patient's femoral mechanical axis, which connects the center of the patient's hip with the center of the patient's knee. In this embodiment, the navigation system's software can identify the mechanical axis and projects its image on a computer generated image of the femur. No matter how surgical site 736a is determined, however, if it is later found to be inappropriate for conducting the surgery (i.e., too medial or central), surgeon 718 is always able to override the site and rely on the computer for orientation only (parallel to the mechanical axis).

In the system of the present disclosure, the various projectors of surgical navigation system 20 can be used to project different indicia onto the surgical site at various stages of the procedure, which can provide precise orientation and position information for surgical instruments, such as those located in tray 48 (FIG. 1). For example, once drill guide 710 is located at surgical target site 736a, a drill location icon (not shown) can be projected onto femur 722 using beam 742 of projector 702, thereby prompting surgeon 718 to drill into bone 722 with surgical drill 738. Simultaneously, as will be discussed below in greater detail, a projector (such as projector 22C of FIG. 1) can be used to identify surgical drill 738 in tray 34. As surgeon 718 aligns drill guide 710 with surgical target site 736a by using surgical navigation technology, the use of invasive instruments and/or IM referencing guides can be avoided. Surgical navigation system 20 can also project other indicia such as resection planes, preoperatively planned landmarks, alignment axes.

In further examples, projectors can be used to assist surgeon 718 in adjusting the position of various tools or instruments to perform the procedure. For example, as discussed above, surgeon 718 may need to move drill guide 710 immediately to the right along line 739 to align drill location icon 737 with surgical target site 736a. Thus, with reference to computer display 724, arrow 744 can be displayed to prompt surgeon 718 to physically move drill guide 710 to the right. Beam 742 can also simultaneously project a similar arrow onto bone 722, although not shown in FIG. 3 for clarity.

Projection of the surgical plan onto anatomy of patient 730 can facilitate on-the-fly adjustment of the surgical plan. As projector 702 uses beam 742 to project the next step in a surgical procedure, surgeon 718 can evaluate the judged effectiveness of the next step in the plan based on information gathered in performing the steps of the plan up to that point in time. For example, surgeon 718 can review resection planes for femur 722 and tibia 720 in an image of the anatomy of patient 730 shown on surgical plan image 732, make changes in the location, size and orientation of the resection planes and, generally, work interactively until the pre-operative plan is approved by surgeon 718. In such an example, surgeon 718 may notice that an anatomic landmark expected to be in a particular position is off relative to beam 742 and, as such, surgeon 718 can correspondingly adjust the location of drill location icon 737 manually or simply manually offset the position of drill guide 710 an amount corresponding to the difference between the expected location and the actual location of the anatomic landmark.

With the systems and methods described herein, surgeon 718 is better able to perform surgical operations. In particular, the entire surgical procedure can be more accurately and more rapidly completed, as each successive step can be completed in in less time and with more precision. The use of projectors described herein may also simplify surgical procedures, such as by eliminating the need for intramedullary rods typically used for alignment of drill guides and the like. Thus, the faster, simpler techniques described herein can reduce the cost associated with surgical procedures by reducing time spend in the operating room and the use of expensive surgical instruments.

Figure 4:
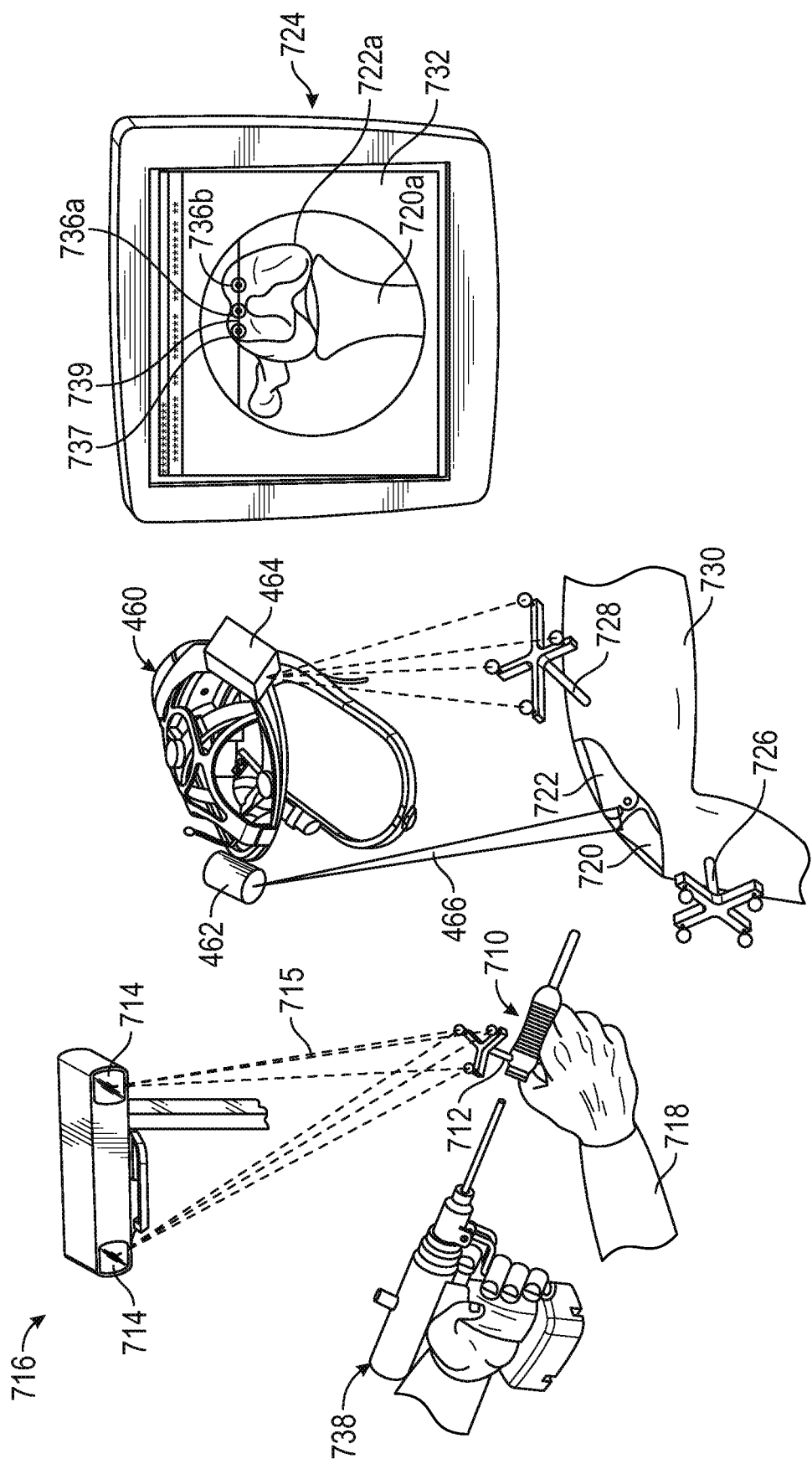
FIG. 4 is a schematic view of a helmet-mounted projector used in conjunction with a helmet-mounted optical locator.

FIG. 4 is a schematic view of a navigation system (e.g. navigation system 20 of FIG. 1) having helmet 460, helmet-mounted projector 462 and helmet-mounted optical locator 464. The navigation system of FIG. 4 can include the same components as those shown in FIG. 3, with helmet 460, projector 462 and optical locator 464 replacing projector 702.

One example of a surgical helmet suitable for use with the present disclosure is described in U.S. Pub. No. 2015/0090254 to Pavalarajan et al., which is hereby incorporated herein in its entirety by this reference. In one example, projector 462 can comprise a so-called pico projector, or pocket projector, which may be any hand-held sized, commercially available projector capable of emitting a light source, such as a laser or LED light. Optical locators 716 and 464 can operate to determine the three-dimensional position of arrays 712, 726 and 728 within operation room 10 (FIG. 1) as has been described herein.

Locating optical locator 464 directly on helmet 640 can ensure that arrays within the field of view of surgeon 718 will always be recognized by the navigation system, thus allowing the navigation system to be looking up information relevant to those arrays, and the instruments and tools connected to those arrays, in the aforementioned matrix. Locating projector 462 directly on helmet 640 can ensure that the instructions generated by beam 466 will always remain in the field of view of surgeon 718 and that the orientation of the instructions will be correlated to the point of view of surgeon 718, e.g. any letters or text produced by beam 466 will not be upside down.

Projector 462 can use beam 466 to project various instructions from the surgical plan based on, for example, the instrument surgeon 718 is holding in his or her hand, such as drill guide 710 in the illustrated example. The instructions depicted by beam 466 can include various landmarks, alignment axis, and resection planes onto bones 720, 722 of patient 730, as discussed above. Thus, projector 462 can operate similarly to projector 702 of FIG. 3 to provide visual instructions to surgeon 718 based on the surgical plan using information stored in the navigation system for each tool or instrument based on the location of each tool or instrument determined by optical locator 464 or 716 and the appropriately correlated array for that particular tool or instrument.

Figure 5:
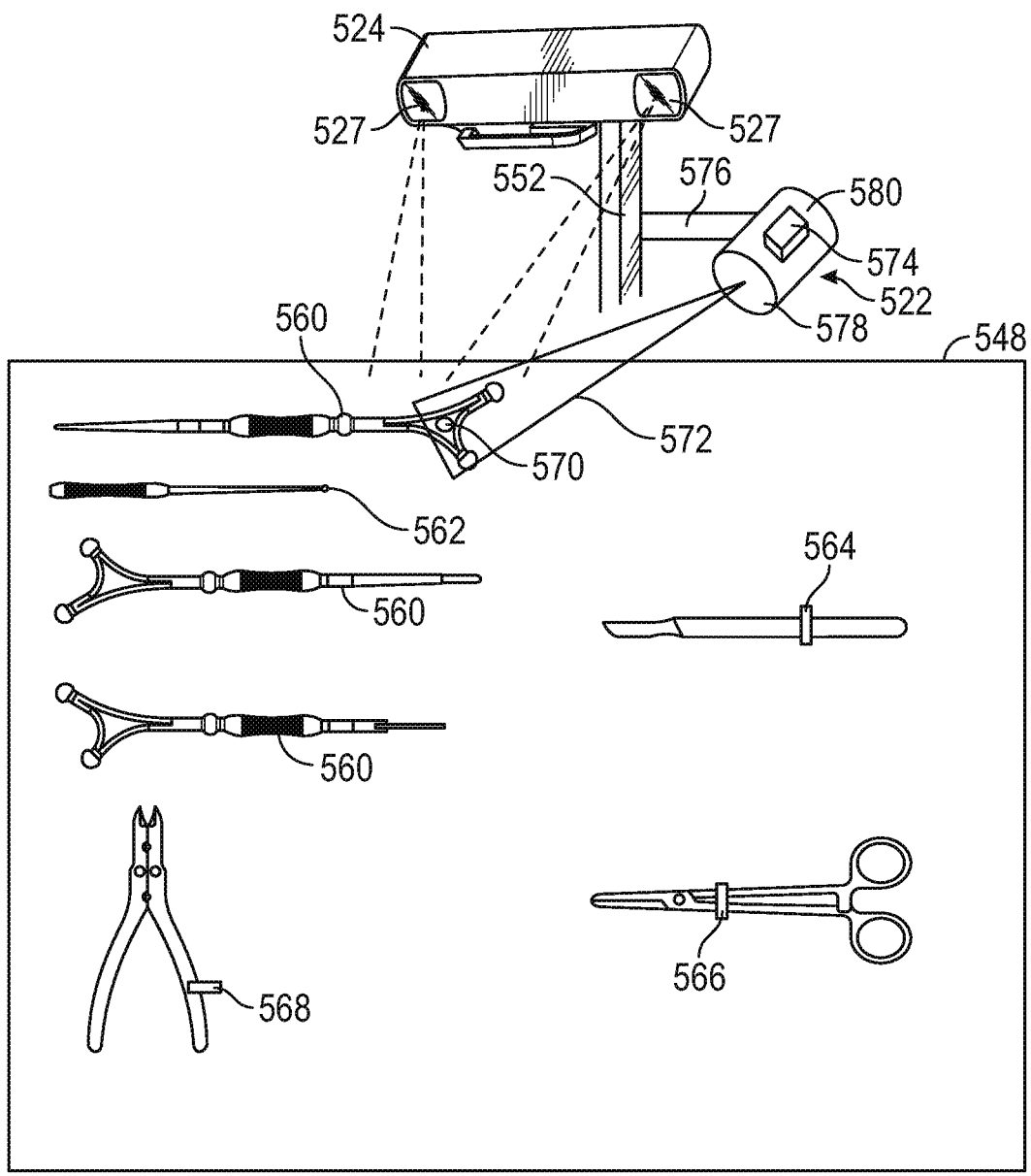
FIG. 5 is a schematic view of a surgical tray having a projector used in conjunction with an optical locator.

FIG. 5 is a schematic view of surgical tray 548 (e.g. tray 48 of FIG. 1) having projector 522 (e.g. projector 22c of FIG. 1) being used in conjunction with optical locator 524 (e.g. optical locator 24 of FIG. 1). Tray 548 can be stocked with various surgical instruments and tools, such as probes 560, stylus 562, scalpel 564, forceps 566 and cutting tool 568. Projector 522 can generate various instructions or indicia, such as icon 570, using beam 572. Projector 522 can additionally be equipped with microphone 574, which can be connected to navigation system 20 to trigger generation of icon 570 with beam 572 based on voice commands.

Projector 522 can be programmed to generate beam 752 based on various prompts from the navigation system. In one example, the navigation system recognizes the step in the surgical plan that needs to be performed next based on the collective position of the instruments and tools being used at that point in time. For example, an optical locator, such as optical locator 24 of FIG. 1, may identify that surgical drill 50 is being used and thus may subsequently determine that probe 560 needs to be used next to confirm the formation of the drilled hole based on information provided in the aforementioned matrix. Thus, projector 522 can display icon 570 on probe 560 to indicate that clinician 14 needs to provide that tool to surgeon 718.

In other examples, projector 522 can be prompted to identify probe 560 using voice recognition and microphone 574. When surgeon 718 calls for a particular instrument or tool by audibly vocalizing the particular, unique name of the instrument, microphone can pick up the voice sound and compare the associated voice pattern to pre-obtained, sound patterns stored in the matrix. Once identified, projector 522 can direct beam 574 onto the instrument associated with the stored sound pattern. For example, projector 522 can shape beam 572 to generate icon 570 on probe 560. In one example, icon 570 simply comprises a dot or another simple shape that draws the attention of clinician 14, in this case a scrub tech, to the desired tool. In another example, icon 570 can comprise a lit-up image having the profile of the tool or instrument that can either be projected directly onto the tool or instrument to highlight it or projected onto a surface to show clinician 14 the shape of the tool or instrument to look for in tray 548.

Projector 522 can also identify any corresponding pieces or instrument components that need to be assembled to the main instrument identified by beam 572. Additionally, projector 522 can be used to direct the clinician or surgeon to proper location within tray 548 to return tools and instruments that are no longer needed or that need to be returned to tray 548 for whatever reason.

In a typical situation, the tool or instrument will be identified in tray 548. However, projector 522 can be configured to illuminate tools and instruments located in different locations in operating room 10, such as those being used at the surgical site near bones 720 and 722. To that end, projector 522 can be mounted to optical 524 in a moveable fashion. For example, projector 522 can be connected to stand 552 using motor mount 576. Motor mount 576 can include an electric motor in a housing that permits the orientation of projector 522 relative to stand 552 to be altered in order to direct beam 572 to different locations on tray 548 or operating room 10. In other examples, lens 578 of projector 522 can be moveable within housing 580 of projector 522 in order to change the direction of beam 572. In other examples, motor mount 576 can simply comprise, or be replaced with, a fixed connector rigidly connecting projector 522 and stand 552.

Navigation system 20 can recognize the location of each tool or instrument using arrays, such as arrays 26A-26, 712, etc., so that navigation system 20 can know where to direct beam 572. In another example, navigation system 20 can use the known location of the tool or instrument based on the steps or point in the surgical plan that has been performed so far. In another example, the location of each tool or instrument can be determined using cameras 527 of optical locator 524. Cameras 527 can be used to recognize the shape or outline of each tool or instrument in tray 548. Additionally or alternatively, cameras 527 can be used to recognize a unique identifier on each tool or instrument, such as a bar code, Quick Response (QR) code, or another such tag or label. The unique shape, outline, identifier, tag or label for each specific tool or instrument can be stored in the matrix for cross-referencing to other data relating to each specific tool or instrument.

In conventional surgical systems, it can sometimes be difficult for operating room surgical personnel to locate the proper tool within one or more surgical trays promptly and accurately. Different types of instruments are sometimes provided with color-coding, but such coding can sometimes be of insufficient helpfulness when various instruments have very similar shapes. In the system of the present application, projector 522 can project identification icon 570 directly onto an instrument in tray 548 using beam 572. This can allow clinician 14 to remain mentally focused on the surgical procedure and increase identification speeds (i.e. reduce time spent looking for the needed instrument) of clinician 14, thereby reducing potentially expensive operating room time and cost. Additionally, the system of the present application can reduce the number of personnel present in the operating room, such as by eliminating the need for sales representatives to be in the operating room to assist clinician 14 in identifying new or unfamiliar instruments, which can reduce the number of people that need to be gowned, scrubbed and otherwise sterilized or sanitized.

Figure 6:
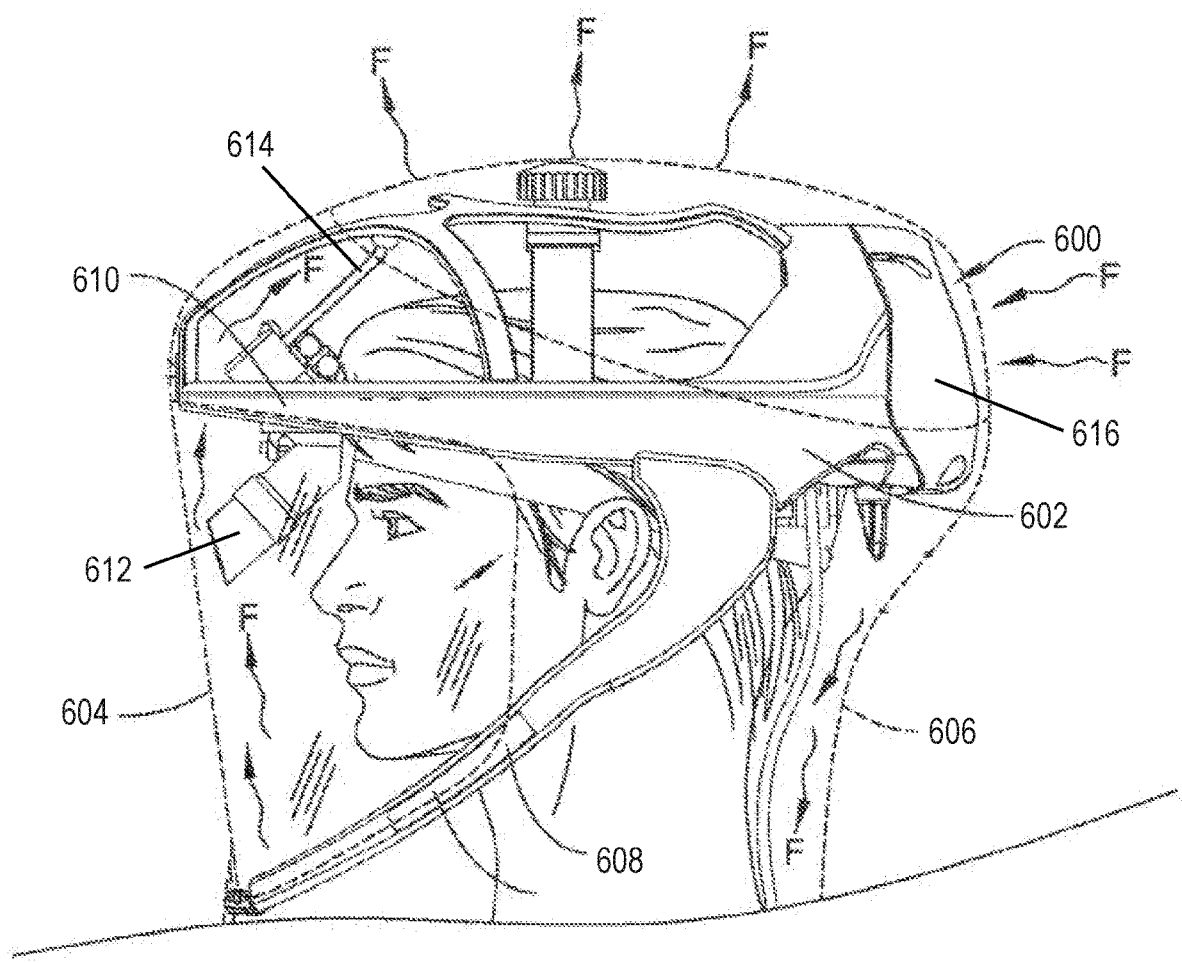
FIG. 6 is a side view of a surgical helmet comprising a cage, a face shield and a hood.

FIG. 6 illustrates helmet 600 comprising cage 602, face shield 604 and hood 606. Cage 602 can comprise an open lattice framework or open cage. Cage 602 can comprise chin bar 608 and brow bar 610. Illumination light source 612 can be mounted to cage 602. Illumination light source 612 can be mounted to brow bar 610 at a pivoting connection and can be pivoted by actuation of lever 614. Air flow F can move through helmet 600, such as via operation of fan 616. Helmet 600 can include features of the present disclosure, such as projector 462, optical locator 464, a microphone and the like.

VARIOUS NOTES & EXAMPLES

Example 1 can include or use subject matter such as a surgical navigation system comprising: a computer system that can have stored therein instructions for performing a surgical plan; a tracking system electronically connected to the computer system, the tracking system having a viewing area in which markers can be located within a three-dimensional space relative to the viewing area; and a projector electronically connected to the computer system, the projector can have a beam projectable into the viewing area to display a step of the surgical plan based on a location of a marker in the three-dimensional space.

Example 2 can include, or can optionally be combined with the subject matter of Example 1, to optionally include an instrument that can have an associated marker trackable by the tracking system within the viewing area, wherein the surgical plan can provide a positional instruction for the instrument within the three-dimensional space based on a location of the associated marker in the three-dimensional space.

Example 3 can include, or can optionally be combined with the subject matter of one or any combination of Examples 1 or 2 to optionally include a display that simultaneously visualizes the surgical plan.

Example 4 can include, or can optionally be combined with the subject matter of one or any combination of Examples 1 through 3 to optionally include a surgical plan that can comprise: images of a surgical site of a patient; measurements of a bone in the surgical site; and locations of instruments to be positioned relative to the bone during a procedure.

Example 5 can include, or can optionally be combined with the subject matter of one or any combination of Examples 1 through 4 to optionally include a displayed step of the surgical plan of the projector including indicia projected onto the bone indicating where an instrument should be located.

Example 6 can include, or can optionally be combined with the subject matter of one or any combination of Examples 1 through 5 to optionally include a projector that can be mounted in the three-dimensional space on a stand.

Example 7 can include, or can optionally be combined with the subject matter of one or any combination of Examples 1 through 6 to optionally include a projector that can be mounted on a helmet to be worn by a person performing at least a portion the surgical plan.

Example 8 can include, or can optionally be combined with the subject matter of one or any combination of Examples 1 through 7 to optionally include a projector that can be mounted on a surgical cart and can identify an instrument from a plurality of instruments located in a tray to be used by a surgeon to perform a step in the surgical plan.

Example 9 can include, or can optionally be combined with the subject matter of one or any combination of Examples 1 through 8 to optionally include a computer system that can include data identifying the plurality of instruments and the tracking system can recognize the plurality of instruments based on geometries of the instruments.

Example 10 can include, or can optionally be combined with the subject matter of one or any combination of Examples 1 through 9 to optionally include a computer system that can include data identifying the plurality of instruments and the tracking system can recognize the plurality of instruments based on a unique marking on each instrument.

Example 11 can include, or can optionally be combined with the subject matter of one or any combination of Examples 1 through 10 to optionally include a computer system that can include a voice recognition component that can be configured to hear a surgeon calling for a particular instrument and that can send an instruction to the projector to identify the particular instrument with the beam.

Example 12 can include, or can optionally be combined with the subject matter of one or any combination of Examples 1 through 11 to optionally include a projector that can project a beam recognizable by the tracking system.

Example 13 can include or use subject matter such a method for guiding a surgical instrument, the method can comprise: tracking a surgical instrument within a three-dimensional space using a computer-operated tracking system; matching the surgical instrument to a step in a surgical plan for conducting the surgical procedure using the surgical instrument; and projecting a visual instruction into the three-dimensional space for the step in the surgical plan related to the instrument.

Example 14 can include, or can optionally be combined with the subject matter of Example 13, to optionally include utilizing a camera to recognize a specific instrument from a plurality of instruments in a tray corresponding to the step of the surgical plan.

Example 15 can include, or can optionally be combined with the subject matter of one or any combination of Examples 13 or 14 to optionally include a visual instruction that can comprise projecting an identifying marker onto the specific instrument in the tray.

Example 16 can include, or can optionally be combined with the subject matter of one or any combination of Examples 13 through 15 to optionally include a camera that can recognize an outline of the specific instrument.

Example 17 can include, or can optionally be combined with the subject matter of one or any combination of Examples 13 through 16 to optionally include a camera that can recognize a unique visual tag located on the specific instrument.

Example 18 can include, or can optionally be combined with the subject matter of one or any combination of Examples 13 through 17 to optionally include a visual instruction that can comprise projecting a directional movement instruction for the surgical instrument onto a patient.

Example 19 can include, or can optionally be combined with the subject matter of one or any combination of Examples 13 through 18 to optionally include projecting the visual instruction from a helmet-mounted projector.

Example 20 can include, or can optionally be combined with the subject matter of one or any combination of Examples 13 through 19 to optionally include projecting the visual instruction from a stand-mounted projector.

Example 21 can include, or can optionally be combined with the subject matter of one or any combination of Examples 13 through 20 to optionally include projecting the visual instruction in response to an audio call.

Example 21 can include, or can optionally be combined with the subject matter of one or any combination of Examples 13 through 21 to optionally include tracking anatomy of a patient using the computer-operated tracking system to align projection of the visual instruction of the surgical plan.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A surgical helmet comprising:
    a cage for positioning on a head of a user;
    a face shield mountable to the cage and through which the user can see when wearing the surgical helmet;
    a hood couplable to the cage and face shield to cover the head, wherein the hood, the face shield and the cage define a field of view for the user;
    a locator mounted to the surgical helmet, the locator configured to have a viewing area in which positions of navigation markers for a surgical navigation system can be determined within a three-dimensional space of the surgical navigation system relative to the viewing area for recognition by the locator;
    a projector mounted to the surgical helmet via an electric motor, wherein the projector is configured to project a beam of visible indicia into the field of view to convey an instruction for a surgical procedure and the electric motor can change a trajectory of the beam relative to the field of view;
    a microphone mounted to the surgical helmet to control operation of the projector; wherein the viewing area is coincident with the field of view;
    a memory device located on the surgical helmet and in communication with the projector, the locator and the microphone, the memory device including a surgical plan listing instruments used in the surgical procedure, locations for use of the instruments in the three-dimensional space, a voice recognition signature for each instrument of the instruments, and indicia for each instrument of the instruments to be generated by the visible indicia of the projector; and a processor device located on the surgical helmet and in communication with the projector, the locator, the microphone and the memory device, the processor device configured to:

determine three-dimensional positions of the navigation markers in the field of view using the locator; and direct the projector and the electric motor to generate the beam to transmit the indicia into the three-dimensional space in the field of view at a location for a specific instrument of the instruments for which the microphone received a voice recognition signature using the three-dimensional positions from the surgical plan and determined three-dimensional positions of the instruments determined by the locator when the specific instrument is in the field of view.

2. The surgical helmet of claim 1, wherein the locator and the projector are mounted on opposite sides of a brow bar of the cage.

3. The surgical helmet of claim 1, further comprising a fan to drive cooling air through at least a portion of the cage.

4. The surgical helmet of claim 1, further comprising:
an electronic control module mounted to the cage to operate functions of the surgical helmet; and
a power source mounted to the cage.

5. The surgical helmet of claim 4, further comprising a speaker configured to generate an audible tone indicative of a status of the surgical helmet.

6. The surgical helmet of claim 1, further comprising a heads-up display mounted to the surgical helmet.

7. The surgical helmet of claim 1, wherein the projector comprises a pico-projector capable of emitting laser or LED light as the beam.

8. The surgical helmet of claim 1, wherein the beam is identifiable by a surgical tracking system so that the projector can change the location of the beam in real time based on feedback from the tracking system.

9. The surgical helmet of claim 1, wherein the locator is configured to triangulate position of a navigation maker.

10. The surgical helmet of claim 9, wherein the locator comprises at least two charge couple device cameras.

11. The surgical helmet of claim 9, wherein the locator comprises an electromagnetic tracking system.

12. The surgical helmet of claim 1, wherein the projector is mounted to the surgical helmet via an electric motor that can change a trajectory of the beam relative to the field of view.

13. The surgical helmet of claim 1, further comprising:
an illumination light source mounted to the cage via a pivoting mechanism, wherein beam of indicia that is projected from the projector is visible within light from the illumination light source; and
a lever for actuating the pivoting mechanism of the illumination light source.

14. The surgical helmet of claim 13, wherein the illumination light source is configured to emit light to illuminate the three-dimensional space.

15. A surgical helmet comprising:
a cage for positioning on a head of a user;
a face shield mountable to the cage to define a field of view for the user;
an illumination light emitter mounted to the surgical helmet;
a projector mounted to the surgical helmet via an electric motor, wherein the projector is configured to project a beam of visible indicia into the field of view to convey an instruction for a surgical procedure and the electric motor can change a trajectory of the beam relative to the field of view;
a microphone mounted to the surgical helmet to control activation of the projector;
a locator mounted to the surgical helmet, the locator configured to have a viewing area in which positions of navigation markers for a surgical navigation system can be triangulated within a three-dimensional space of the surgical navigation system, the locator configured to control a trajectory of the visible indicia of the projector;
a memory located on the surgical helmet and device in communication with the projector, the locator and the microphone, the memory device including a surgical plan listing instruments used in the surgical procedure, locations for use of the instruments in the three-dimensional space, a voice recognition signature for each instrument of the instruments, and indicia for each instrument of the instruments to be generated by the visible indicia of the projector; and
a processor device located on the surgical helmet and in communication with the projector, the locator, the microphone and the memory device, the processor device configured to:
determine three-dimensional positions of the navigation markers in the field of view using the locator; and
direct the projector and the electric motor to generate a beam that transmits the indicia into the three-dimensional space in the field of view at a location for a specific instrument of the instruments for which the microphone received a voice recognition signature using the three-dimensional positions from the surgical plan and determined three-dimensional positions of the instruments determined by the locator when the specific instrument is in the field of view.

16. The surgical helmet of claim 15, wherein:
the visible indicia comprises a cutting plane or an alignment axis for a specific instrument on a patient, the visible indicia being projectable onto anatomy of the patient; and
the locator and projector are positioned on the helmet to simultaneously interact with a field-of-view of the user.

17. The surgical helmet of claim 15, wherein the processor device is further configured to recognize the presence of the specific instrument in hands of the user and automatically project the indicia onto the anatomy.

* * * * *